(12) United States Patent
Bauman et al.

(10) Patent No.: US 11,041,836 B2
(45) Date of Patent: Jun. 22, 2021

(54) CATALYST GUARD

(71) Applicant: O.I. Corporation, College Station, TX (US)

(72) Inventors: Noel C. Bauman, College Station, TX (US); James G. Slaton, College Station, TX (US); Joan Zarate Killgore, Iola, TX (US)

(73) Assignee: O.I. CORPORATION, College Station, TX (US)

( * ) Notice: Subject to any disclaimer, the term of this patent is extended or adjusted under 35 U.S.C. 154(b) by 150 days.

(21) Appl. No.: 15/806,597

(22) Filed: Nov. 8, 2017

(65) Prior Publication Data

US 2018/0321203 A1    Nov. 8, 2018

Related U.S. Application Data

(60) Provisional application No. 62/418,916, filed on Nov. 8, 2016.

(51) Int. Cl.
*G01N 31/12* (2006.01)
*G01N 33/18* (2006.01)
(Continued)

(52) U.S. Cl.
CPC .............. *G01N 31/12* (2013.01); *B01L 3/04* (2013.01); *F27B 17/02* (2013.01);
(Continued)

(58) Field of Classification Search
CPC ........... G01N 33/1826; G01N 33/1846; G01N 31/12; F27B 17/02
See application file for complete search history.

(56) References Cited

U.S. PATENT DOCUMENTS

| 1,903,036 A | 3/1933 | Francis |
| 2,215,081 A | 9/1937 | Hess |

(Continued)

FOREIGN PATENT DOCUMENTS

| GB | 2447707 B | 11/2009 |
| KR | 101612614 B1 | 4/2016 |
| WO | 03023364 A2 | 3/2003 |

OTHER PUBLICATIONS

"Quartz Furnace Tubes," GreatGlas, greatglas.com, dated Dec. 12, 16-May 16, 20 printed Jan. 2017. http://web.archive.org/web/20121216035131/http://www.greatglas.com/QuartzFurnaceTubes.htm.

(Continued)

*Primary Examiner* — Steven S Anderson, II
(74) *Attorney, Agent, or Firm* — Ware, Fressola, Maguire & Barber LLP

(57) ABSTRACT

A furnace system features a combination of a furnace, a main combustion furnace tube and a disposable guard tube. The main combustion furnace tube is configured to couple and extend from the furnace, made of a quartz tube material, and has a zone for a combustion catalyst or high temperature support configured or formed therein. The disposable guard tube is coupled to the main combustion furnace tube, has a top opening configured to receive and have direct exposure to a liquid sample being injected into the main combustion furnace tube, and also has a bottom opening to provide the liquid sample to the main combustion furnace tube for processing in the zone for the combustion catalyst or high temperature support.

14 Claims, 5 Drawing Sheets

Main combustion furnace tube 30

(51) Int. Cl.
  *B01L 3/04* (2006.01)
  *F27B 17/02* (2006.01)
(52) U.S. Cl.
  CPC ..... *G01N 33/1826* (2013.01); *G01N 33/1846* (2013.01); *B01L 2300/0832* (2013.01)

(56) References Cited

U.S. PATENT DOCUMENTS

| | | | |
|---|---|---|---|
| 2,332,943 | A | 10/1943 | Sobers |
| 2,931,636 | A | 4/1960 | Engelhard |
| 3,923,464 | A | 12/1975 | Sitek et al. |
| 4,243,477 | A | 1/1981 | Broberg et al. |
| 4,280,656 | A | 7/1981 | Swanson |
| 4,344,917 | A * | 8/1982 | Schorno .............. G01N 30/12 422/606 |
| 4,440,595 | A | 4/1984 | Broberg |
| 4,784,833 | A | 11/1988 | Martin et al. |
| 4,803,051 | A * | 2/1989 | Knapp .................. G01N 21/71 356/315 |
| 5,109,710 | A * | 5/1992 | Newkirk .............. G01N 30/12 73/23.41 |
| 5,110,554 | A | 5/1992 | Tanimoto |
| 5,130,104 | A | 7/1992 | Morris |
| 5,133,533 | A | 7/1992 | Herchenroeder |
| 5,236,353 | A | 8/1993 | Adani et al. |
| 5,246,667 | A | 9/1993 | Hemzy et al. |
| 5,567,388 | A | 10/1996 | Morita et al. |
| 5,578,132 | A | 11/1996 | Yamaga et al. |
| 6,013,158 | A | 1/2000 | Wootten |
| 6,101,844 | A | 8/2000 | Fowler et al. |
| 7,108,746 | B2 | 9/2006 | Zehavi et al. |
| 7,497,991 | B2 | 3/2009 | Rohaly et al. |
| 8,377,397 | B2 | 2/2013 | Ford |
| 2005/0270895 | A1 | 12/2005 | Strang |
| 2016/0319566 | A1 | 11/2016 | Carter et al. |

OTHER PUBLICATIONS

"Inner Combustion Tube Silica CHN-1000 608-342," Elemental Microanalysis, elementalmicroanalysis.com, Catalogue Code: C4053, printed Jan. 2017. http://www.elementalmicroanalysis.com/product_details.php?product=C4053&cdescription=Inner%20Combustion%20Tube%20Silica%20CHN-1000%20%20608-342%20&sub=Quartz,%20Glassware%20and%20Furnace%20Tubes&category=143&menu=.

Bates, Stephen C., "High temperature transparent furnace development," printed Jan. 2017. http://www.tvu.com/PHighTTFweb.html.

English language abstract of KR101612614.

* cited by examiner

Figure 1: Furnace system 10

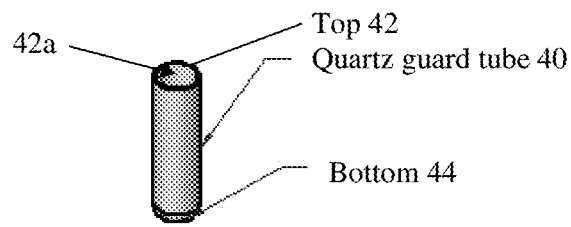
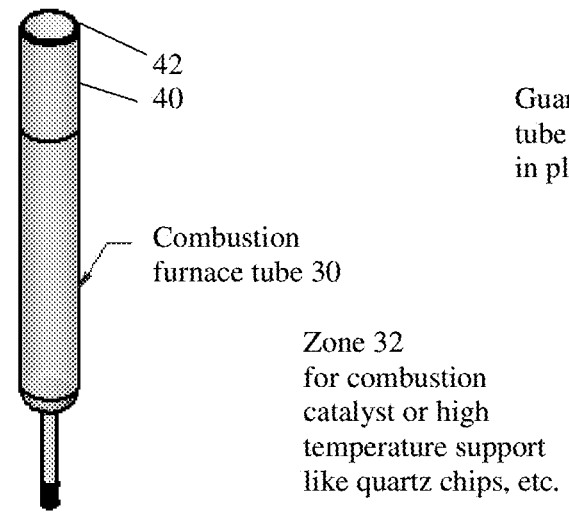
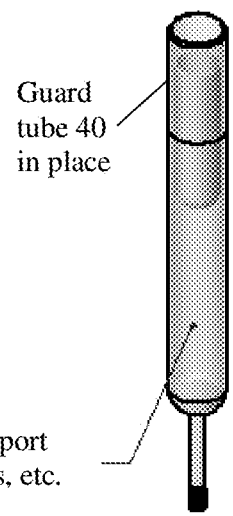
Figure 2

Fig. 3A
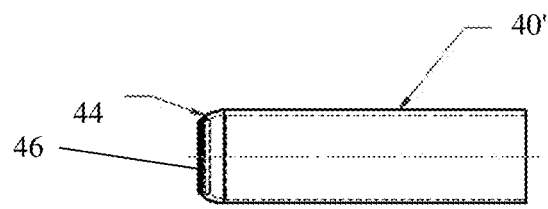
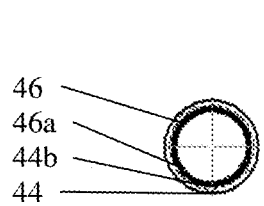        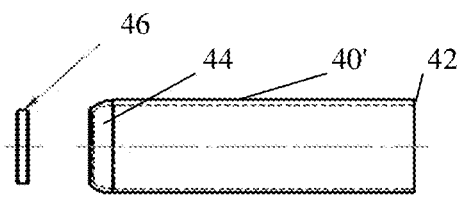
Fig. 3C              Fig. 3B
Figure 3: Disposable guard tube 40' with Frit 46

Fig. 4A
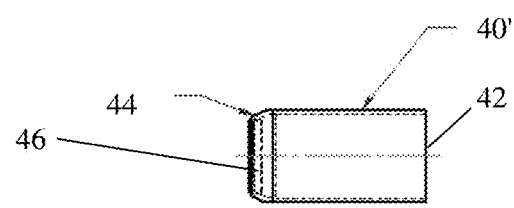
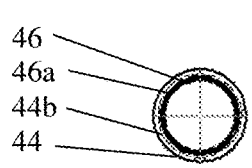
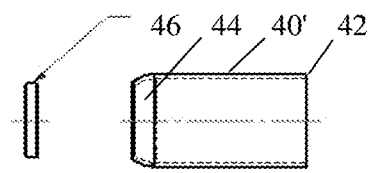
Fig. 4C
Fig. 4B
Figure 4: Disposable guard tube 40' with Frit 46

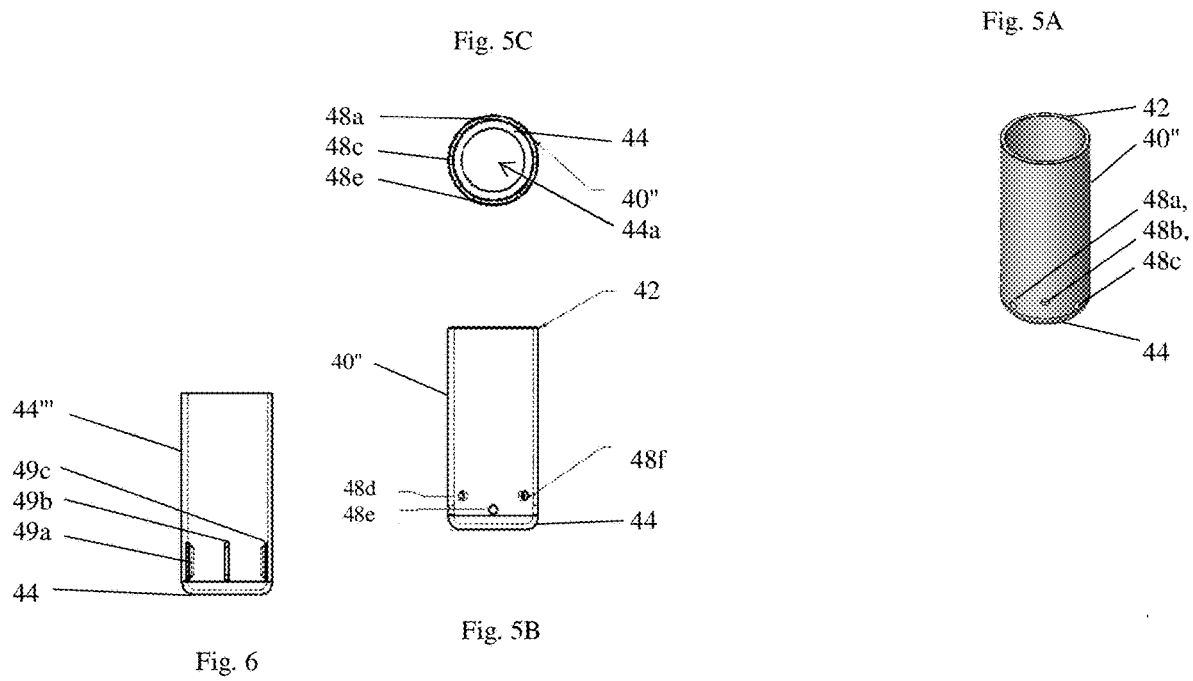
Figure 5: Disposable guard tube 40" with Holes (Figs 5A-5C)

CATALYST GUARD

CROSS-REFERENCE TO RELATED APPLICATIONS

This application claims benefit to provisional patent application Ser. No. 62/418,916 (911-027.1-1/N-OIC-0018US), filed 8 Nov. 2016, which is incorporated by reference in its entirety.

BACKGROUND OF THE INVENTION

1. Field of Invention

This invention relates to a Total Organic Carbon (TOC) system for measuring organic contaminants in a water system; and more particularly relates to a main combustion furnace tube in such a TOC system.

2. Description of Related Art

One issue that is typical with all combustion Total Organic Carbon (TOC) systems is the expense and time involved in maintaining and or replacing the main combustion furnace tube. This is typically due to either chemical attack on the quartz tube material, or eventual structural failure of the tube due to direct exposure to the liquid sample injected. Thus, any design change that can extend the life of these expensive main furnace tubes can offer value to the customer, if it can be done easily and inexpensively.

In view of this, there is a need in the art for a better main combustion furnace tube.

SUMMARY OF THE INVENTION

In summary, the invention utilizes a simple cylindrical tube, typically made of quartz, to serve as a sacrificial surface which the liquid sample can preferentially attack, without interfering with the nominal performance of the TOC analyzer. The most basic and preferred version of the invention is a plain cylinder with openings on each end.

However, other versions of the design could utilize a closed, or semi-closed bottom, with or without ventilation holes and/or slits in the side walls of the cylinder.

The bottom of the cylinder could also be closed using a porous frit, again typically made of quartz. This would be an excellent solution, but at significant expense per part for this disposable guard tube.

According to some embodiments, and by way of example, the present invention may include, or take the form of, a furnace system, featuring a combination of a furnace, a main combustion furnace tube and a disposable guard tube.

The main combustion furnace tube may be configured to couple and extend from the furnace, having a zone for a combustion catalyst or high temperature support configured or formed therein.

The disposable guard tube may be coupled to the main combustion furnace tube, have a top opening configured to receive and have direct exposure to a liquid sample being injected into the main combustion furnace tube, and also have a bottom opening to provide the liquid sample to the main combustion furnace tube for processing in the zone for the combustion catalyst or high temperature support.

The furnace system may include one or more of the following additional features:

The furnace system may include, or form part of, a total organic carbon (TOC) system for measuring organic contaminants in a water system.

The disposable guard tube may be a cylindrical tube made of quartz, or is made of a quartz tube material.

The disposable guard tube may include a closed or semi-closed bottom.

The closed or semi-closed bottom is configured or formed with ventilation holes.

The closed or semi-closed bottom may be configured or formed with slits in side walls of the cylindrical tube.

The closed or semi-closed bottom may be configured or formed using a porous frit, including made from quartz.

The porous frit may be a mixture of silica and fluxes that is fused at high temperature to make glass.

BRIEF DESCRIPTION OF THE DRAWING

The drawing, which are not necessarily drawn to scale, includes FIGS. 1-6, as follows:

FIG. 1A shows a perspective view of a furnace system including a furnace having a main combustion tube with a disposable guard tube arranged thereon, and where FIG. 1B shows a corresponding perspective view of the furnace system in FIG. 1A, e.g., showing a partial exploded view of the main combustion tube and disposable guard tube above and outside of the furnace, all according to some embodiments of the present invention.

FIG. 2 includes FIGS. 2A, 2b and 2C, where FIG. 2A shows a perspective view of a main combustion tube with a disposable guard tube arranged thereon, where FIG. 2B shows a corresponding perspective view of the main combustion tube, the disposable guard tube arranged thereon, and a zone contained or formed therein for combustion catalyst or high temperature support, and FIG. 2C shows a perspective view of the disposable guard tube shown in FIGS. 2A and 2B, all according to some embodiments of the present invention.

FIG. 3 includes FIGS. 3A, 3B and 3C, where FIG. 3A shows a side view of a main combustion tube having a disposable guard tube arranged thereon with a frit coupled inside the bottom of the disposable guard tube, where FIG. 3B shows an exploded view of that shown in FIG. 3A with the main combustion tube and the disposable guard tube coupled together and the frit de-coupled from inside the bottom of the disposable guard tube, and FIG. 3C shows a bottom view of the disposable guard tube shown in FIG. 3A along its longitudinal axis with the frit coupled inside the bottom of the disposable guard tube, all according to some embodiments of the present invention.

FIG. 4 includes FIGS. 4A, 4B and 4C, where FIG. 4A shows a side view of a main combustion tube having a disposable guard tube arranged thereon with a frit coupled inside the bottom of the disposable guard tube, where FIG. 4B shows an exploded view of that shown in FIG. 4A with the main combustion tube and the disposable guard tube coupled together and the frit de-coupled from inside the bottom of the disposable guard tube, and FIG. 4C shows a bottom view of the disposable guard tube shown in FIG. 4A along its longitudinal axis with the frit coupled inside the bottom of the disposable guard tube, all according to some embodiments of the present invention.

FIG. 5 includes FIGS. 5A, 5B, 5C, where FIG. 5A shows a perspective view of a disposable guard tube having a bottom portion with holes configured or formed therein next to its bottom, where FIG. 5B shows a side view of the disposable guard tube shown in FIG. 5A having the bottom portion with the holes configured or formed therein next to its bottom, and where FIG. 5C shows a bottom view of the disposable guard tube shown in FIG. 5A along its longitudinal axis thru its bottom, all according to some embodiments of the present invention.

FIG. 6 shows a side view of a disposable guard tube having the bottom portion with slits configured or formed therein next to its bottom, all according to some embodiments of the present invention.

Figure 1:
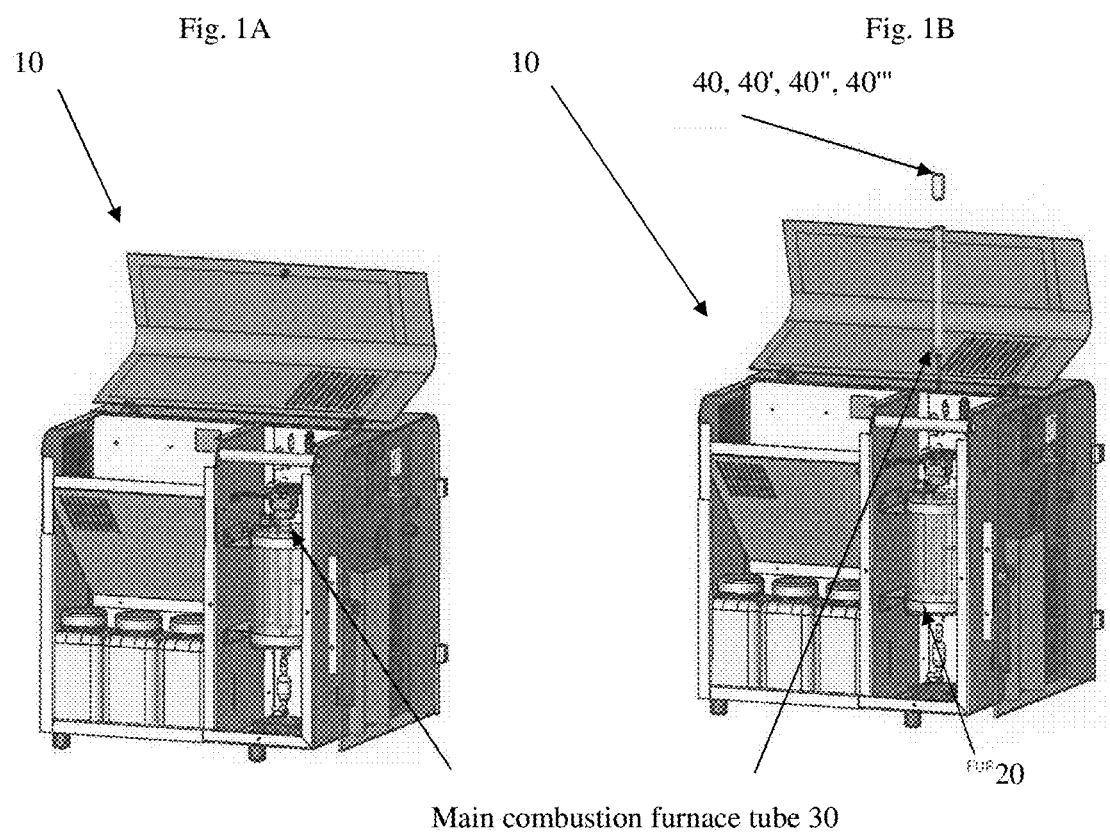
FIG. 1 includes FIGS. 1A and 1B, where

To reduce clutter in the drawing, each Figure in the drawing does not necessarily include every reference label for every element shown therein.

DETAILED DESCRIPTION OF BEST MODE OF THE INVENTION

By way of example, and consistent with that shown in FIGS. 1-6, the present invention may include, or take the form of, a furnace system generally indicated as 10 (e.g., see FIG. 1), featuring a combination of a furnace 20 (FIG. 1), a main combustion furnace tube 30 (e.g., see FIGS. 1 and 2) and a disposable guard tube 40, 40',40", 40'" (e.g., see FIGS. 1-6). By way of example, the furnace system 10 may include, or form part of, a total organic carbon (TOC) system, e.g., for measuring organic contaminants in a water system.

FIGS. 1-2

The main combustion furnace tube 30 may be configured to couple and extend from the furnace 20, may be made of a quartz tube material, and may have a zone 32 for a combustion catalyst or high temperature support configured or formed therein (e.g. like quartz chips). Main combustion furnace tubes like element 30 are known in the art, and the scope of the invention is not intended to be limited to any particular type or kind thereof, e.g., either now known or later developed in the future.

The disposable guard tube 40, 40',40", 40'" may be coupled to the main combustion furnace tube 30, have a top 42 with a top opening 42a configured to receive and have direct exposure to a liquid sample (not shown) being injected, poured or provided into the main combustion furnace tube 30, and also have a bottom or bottom portion 44 with a bottom opening 44a to provide the liquid sample from the disposable guard tube 40, 40',40", 40'" to the main combustion furnace tube 30 for processing in the zone 32 for the combustion catalyst or high temperature support. By way of example, the most basic and preferred version of the disposable guard tube 40 according to present invention is a plain cylinder with top and bottom openings 42a, 44a on each end; however, the bottom 44 of the disposable guard tube 40',40" can be fritted (see FIGS. 3-4), or a bottom portion of the disposable guard tube 40",40'" can be closed ended with holes or slits for gas flow (see FIG. 5-6). In effect, the disposable guard tube 40, 40',40" is an inexpensive disposable part that helps preserve the expensive main combustion furnace tube 30 extending its useful life.

The furnace 20 is configured to heat the liquid sample, e.g., in zones like element 32, for measuring and analyzing the organic contaminants in the water system. As one skilled in the art would appreciate, furnaces like element 20 for heating samples, including furnaces used in TOC systems are known in the art, and the scope of the invention is not intended to be limited to any particular type or kind thereof, e.g., either now known or later developed in the future.

FIGS. 3-4: The Disposable Guard Tune 40' Having Frit 46

FIGS. 3-4 show embodiments of the present invention with the main combustion tube 30 having a disposable guard tube 40' arranged thereon with a porous frit 46 coupled inside the bottom 44 of the disposable guard tube 40'. In FIG. 3, the bottom portion 44 may be configured or formed to receive or accept the frit 46, e.g., by fusing an inside surface 44b of the bottom opening 44a and an outside surface 46a of the frit 46 in multiple places, e.g., including in at least 4 places. As one skilled in the art would appreciate, 100% fusing is not necessary to achieve the desired fusing to implement the present invention.

By way of example, the disposable guard tube 40' may be a cylindrical tube-like structure made of quartz (or a quartz-like material), and the frit 46 may also be a corresponding cylindrical structure also made of quartz (or a quartz-like material) as well. Techniques for fusing two structures together, e.g., such as quartz structures, are known in the art; and the scope of the invention is not intended to be limited to any particular type or kind of fusing technique, e.g., either now known or later developed in the future.

By way of example, the disposable guard tube 40' may be configured with suitable dimensions for coupling to an end of the combustion tube 30, e.g., like that shown in FIG. 2. By way of one particular example, e.g., for one particular application, the dimensions of the disposable guard tube like element 40' may include an 18 mm inner diameter (ID)×20 mm outer diameter (OD). (See the longitudinal dashed lines FIGS. 3A, 3B and 4A, 4B showing the dimension/representation associated with the wall of the disposable guard tube 40'.) By way of one particular example, e.g., for one particular application, the dimensions may include a length of either 2.76+/−0.10 (FIG. 3), or 1.50+/−0.10 (FIG. 4), e.g., including length dimensions measured in centimeters. Depending on the particular application, embodiments having different dimensions may be used in different embodiments/configurations/applications within the spirit of the present invention.

FIG. 5: Disposable Guard Tube 40" Having Holes

FIG. 5 shows a disposable guard tube 40" having the bottom portion 44 with holes, some of which are labeled 48a, 48b, 48c, 48d, 48e, 48f, configured or formed therein for gas flow. The scope of the invention is not intended to be limited to the number of holes, the size/dimension of the holes, the geometric configuration of the holes, the arrangement/configuration (e.g., alternating up/down, circumferential and/or equidistant, etc.) of the holes, etc.; and embodiments are envisioned using other types or kind of of numbers, dimensions, configurations, arrangements, etc. of holes than that disclosed herein within the spirit of the present invention.

FIG. 6: Disposable Guard Tube 40" Having Slits

FIG. 6 shows a disposable guard tube 40'" having the bottom portion 44 slits, some of which are labeled 49a, 49b, 49c, configured or formed therein for gas flow. The scope of the invention is not intended to be limited to the number of slits, the size/dimension of the slits, the geometric configuration of the slits, the arrangement/configuration (e.g., alternating up/down, circumferential and/or equidistant, etc.) of the slits, etc.; and embodiments are envisioned using other types or kind of of numbers, dimensions, configurations, arrangements, etc. of slits than that disclosed herein within the spirit of the present invention.

Alternate Materials

The scope of the invention is intended to include, and embodiments are envisioned using, e.g., alternate materials that could also be used in place of quartz. By way of example, the alternate materials may include high temperature ceramics that could also be used in place of quartz, e.g. thin wall alumina (ranging from mullites to sapphire), titania, or any other material that is stable in a wet oxygen environment at greater than 1000 C. The ceramic carbides, ceramic nitrides, and ceramic borides may also work, but would have to be evaluated for stability and background interferences.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A furnace system, comprising
   a furnace;
   a main combustion furnace tube configured to couple and extend above and outside of the furnace, having a zone for a combustion catalyst or high temperature support configured or formed therein, and having a top furnace tube portion configured to receive a liquid sample for processing in the zone; and
   a disposable guard tube coupled to the main combustion furnace tube, having a top portion with a top opening configured to receive and have direct exposure to the liquid sample being injected into the main combustion furnace tube, and having a bottom portion with a bottom opening and being arranged on the top furnace tube portion of the main combustion furnace tube to provide the liquid sample from the bottom opening of the disposable guard tube into the top furnace tube portion of the main combustion furnace tube for processing in the zone for the combustion catalyst or high temperature support, the disposable guard tube being arranged on top of the main combustion furnace tube and configured to serve as a sacrificial surface which the liquid sample being injected into the main combustion furnace tube can attack.

2. A furnace system according to claim 1, wherein the furnace system is a total organic carbon system for measuring organic contaminants in a water system.

3. A furnace system according to claim 1, wherein the disposable guard tube is a cylindrical tube made of quartz or a quartz tube material.

4. A furnace system according to claim 1, wherein the bottom portion is configured as a closed or semi-closed bottom.

5. A furnace system according to claim 1, wherein the bottom portion is configured or formed with ventilation holes.

6. A furnace system according to claim 1, wherein the bottom portion comprises a cylindrical tube having a cylindrical wall configured or formed with slits.

7. A furnace system according to claim 1, wherein the bottom portion comprises a porous frit, including where the porous frit is made from quartz.

8. A furnace system according to claim 7, wherein the porous frit is made from a mixture of silica and fluxes that is fused at high temperature to make glass.

9. A Total Organic Carbon system for measuring organic contaminants in a water system, comprising
   a furnace;
   a main combustion furnace tube configured to couple and extend from the furnace, having a zone for a combustion catalyst or high temperature support configured or formed therein, and having a top furnace tube portion configured to receive a liquid sample for processing in the zone; and
   a disposable guard tube having a top portion with a top opening configured to receive and have direct exposure to the liquid sample being injected into the top furnace tube portion of the main combustion furnace tube, having a bottom portion with a bottom opening and being arranged on the top furnace tube portion of the main combustion furnace tube to provide the liquid sample from the bottom opening of the disposable guard tube into the top furnace tube portion of the main combustion furnace tube for processing in the zone for the combustion catalyst or high temperature support, the disposable guard tube being a cylindrical tube made of quartz or a quartz tube material and configured to serve as a sacrificial surface which the liquid sample being injected into the main combustion furnace tube can attack.

10. A Total Organic Carbon system according to claim 9, wherein the bottom portion is configured as a closed or semi-closed bottom.

11. A Total Organic Carbon system according to claim 9, wherein the bottom portion is configured or formed with ventilation holes.

12. A Total Organic Carbon system according to claim 9, wherein the bottom portion comprises a cylindrical tube having a cylindrical wall configured or formed with slits.

13. A Total Organic Carbon system according to claim 9, wherein the bottom portion comprises a porous frit, including where the porous frit is made from quartz.

14. A Total Organic Carbon system according to claim 13, wherein the porous frit is made from a mixture of silica and fluxes that is fused at high temperature to make glass.

* * * * *